United States Patent [19]

Matzinger

[11] 4,341,700
[45] Jul. 27, 1982

[54] MONOAZO COMPOUNDS HAVING A SUBSTITUTED 1,2,3-TRIAZOLYL-5 DIAZO COMPONENT RADICAL AND AN UNSUBSTITUTED OR SUBSTITUTED 1,4-PHENYLENE COUPLING COMPONENT RADICAL

[75] Inventor: Peter Matzinger, Zürich, Switzerland

[73] Assignee: Sandoz Ltd., Basel, Switzerland

[21] Appl. No.: 2,085

[22] Filed: Jan. 9, 1979

[30] Foreign Application Priority Data

Jan. 10, 1978 [CH] Switzerland ............... 230/78

[51] Int. Cl.³ .................................. C09B 29/22
[52] U.S. Cl. .................. 260/157; 260/156; 260/158; 260/162; 8/692
[58] Field of Search ............................. 260/157

[56] References Cited

U.S. PATENT DOCUMENTS

| | | | |
|---|---|---|---|
| 3,785,829 | 1/1974 | Fernandez | 96/100 |
| 4,039,539 | 8/1977 | Kuhlthau | 260/157 |
| 4,048,151 | 9/1977 | Henzi | 260/156 |
| 4,051,117 | 9/1977 | Kühlthau et al. | 260/156 X |
| 4,082,740 | 4/1978 | Mohr et al. | 260/157 X |

FOREIGN PATENT DOCUMENTS

| | | |
|---|---|---|
| 1927416 | 12/1970 | Fed. Rep. of Germany . |
| 2357448 | 8/1975 | Fed. Rep. of Germany . |
| 1398366 | 3/1965 | France . |
| 95438 | 2/1973 | German Democratic Rep. . |
| 96708 | 4/1973 | German Democratic Rep. . |

OTHER PUBLICATIONS

"J. Chem. Soc.", ©1970, pp. 230–235.
Hoover et al., "J.A.C.S.", 78, pp. 5832–5836 (1956).

*Primary Examiner*—Paul F. Shaver
*Attorney, Agent, or Firm*—Gerald D. Sharkin; Richard E. Vila; Melvyn M. Kassenoff

[57] ABSTRACT

Compounds of the formula

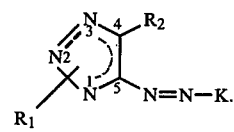

in which $R_1$ is hydrogen or an aliphatic or aromatic substituent conventional for diazo component radicals of disperse dyes and which is bound to a N-atom in the 1- or 2-position of the triazole nucleus through a carbon atom, with the proviso that when $R_1$ is in the 1-position, the broken line represents double bonds in the 2,3- and 4,5-positions and when $R_1$ is in the 2-position, the broken line represents double bonds in the 3,4- and 1,5-positions, $R_2$ is an electron withdrawing or inductive group, and K is a coupling component radical of the aniline series, with the proviso that the molecule is free from cationic groups, sulphonic acid groups, metals and metallizable groups, which compounds are useful as disperse dyes for textile substrates consisting of or comprising synthetic or semi-synthetic, hydrophobic, high molecular weight organic materials such as linear aromatic polyesters, cellulose 2½ acetate, cellulose triacetate and synthetic polyamides.

23 Claims, No Drawings

MONOAZO COMPOUNDS HAVING A SUBSTITUTED 1,2,3-TRIAZOLYL-5 DIAZO COMPONENT RADICAL AND AN UNSUBSTITUTED OR SUBSTITUTED 1,4-PHENYLENE COUPLING COMPONENT RADICAL

The present invention relates to azo compounds, their production and use as disperse dyes.

More particularly, the present invention provides azo disperse dyes of formula I,

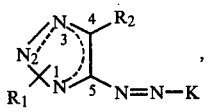

in which
- $R_1$ is hydrogen or an aliphatic or aromatic substituent conventional for diazo components of disperse dyes which substituent is bound to a N-atom in the 1- or 2-position of the triazole nucleus through a carbon atom,
- $R_2$ is an electron withdrawing or inductive group, and
- K is a coupling component radical of the aniline series, with the proviso that the molecule is free from cationic groups, sulphonic acid groups, metals and metallizable groups.

It will be appreciated that substituents or combinations thereof which are known to cause steric or stability problems, e.g.

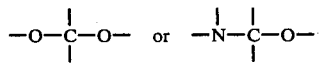

groupings, are not contained in the dye molecule.

The double bonds of the triazole ring are in the 2,3- and 4,5-positions when $R_1$ is in the 1-position and in the 3,4- and 1,5-positions when $R_1$ is in the 2-position.

Preferred aliphatic or aromatic substituents for $R_1$ are those of the alkyl, alkenyl or benzene series.

Preferably $R_1$ is $R_1'$, where $R_1'$ is hydrogen;
alkyl or alkyl monosubstituted by fluorine, bromine, chlorine, hydroxy, alkylcarbonyl, alkoxy, cyano, thiocyano, phenoxy, alkoxycarbonyl, phenoxycarbonyl, alkoxyethoxycarbonyl, aminocarbonyl, alkylaminocarbonyl, dialkylaminocarbonyl, phenylaminocarbonyl, N-alkyl-N-phenylaminocarbonyl, benzoyl, alkylcarbonyloxy, phenylsulphonyl, alkylsulphonyl, aminosulphonyl, alkylaminosulphonyl, dialkylaminosulphonyl, phenylaminosulphonyl, N-alkyl-N-phenylaminosulphonyl or phenyl which is unsubstituted or substituted by up to two substituents independently selected from chlorine, bromine, nitro, cyano, trifluoromethyl, alkyl and alkoxy;
alkenyl or alkenyl monosubstituted by chlorine, bromine or phenyl;
phenyl or phenyl substituted by a total of up to three substituents selected from alkyl, alkoxy, chlorine, bromine, nitro (up to three of each of these) cyano, trifluoromethyl, alkoxycarbonyl (up to two of each of these), formyl, alkylcarbonyl, aminocarbonyl, alkylaminocarbonyl, dialkylaminocarbonyl, alkylsulphonyl, phenylsulphonyl, aminosulphonyl, alkylaminosulphonyl, dialkylaminosulphonyl and phenylaminosulphonyl (up to one of each of these).

Any alkyl or alkoxy moiety as $R_1'$ or contained therein contains up to 4, preferably up to 2, carbon atoms and any alkenyl group contains from 2 to 4, preferably 3 or 4, carbon atoms.

More preferably $R_1$ is $R_1''$, where $R_1''$ is hydrogen; $(C_{1-2})$alkyl; $(C_{1-2})$alkyl monosubstituted by chlorine, phenyl, mono- or dichlorophenyl, cyano, acetoxy, benzoyl, alkyl$(C_{1-2})$carbonyl or aminocarbonyl; allyl; 3-chloroallyl;3-phenylallyl; phenyl; chlorophenyl or tolyl.

Most preferably $R_1$ is $R_1'''$, where $R_1'''$ is phenyl, chlorophenyl, benzyl, mono- or dichlorobenzyl or tolyl, with benzyl and mono- and dichlorobenzyl being especially preferred.

$R_2$ is preferably $R_2'$, where $R_2'$ is cyano, thiocyano, nitro, carboxyl, alkylcarbonyl, benzoyl, alkoxycarbonyl, alkoxyethoxycarbonyl, phenoxycarbonyl, aminocarbonyl, alkylaminocarbonyl, dialkylaminocarbonyl, alkylsulphonyl, phenylsulphonyl, aminosulphonyl, alkylaminosulphonyl, dialkylaminosulphonyl, phenylaminosulphonyl or phenylaminocarbonyl, any alkyl or alkoxy moiety in such substituents containing up to 4, preferably up to 2, carbon atoms.

More preferably $R_2$ is $R_2''$, where $R_2''$ is cyano, nitro, carboxyl, acetyl, alkoxy$(C_{1-2})$carbonyl, aminocarbonyl, thiocyano or methylsulphonyl.

Where a carboxyl group is present, this may be in free acid form or in the form of a salt of a non-chromophoric cation.

Most preferably $R_2$ is $R_2'''$, where $R_2'''$ is cyano, aminocarbonyl or alkoxy$(C_{1-2})$carbonyl, with cyano being especially preferred.

Thus, preferred compounds of formula I are those wherein $R_1$ is $R_1'$, preferably $R_1''$, $R_2$ is $R_2'$, preferably $R_2''$ and K is a coupling component of the aniline series.

Preferably K is K' where K' is

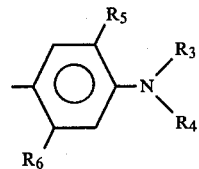

in which each of $R_3$ and $R_4$, independently, is hydrogen; $(C_{1-8})$alkyl; $(C_{1-8})$alkyl monosubstituted by hydroxyl, chlorine, bromine, cyano, thiocyano, alkylcarbonyl, alkoxycarbonyl, formyloxy, alkylcarbonyloxy, chloro- or bromoalkylcarbonyloxy, alkoxycarbonyloxy, alkoxyalkoxycarbonyl,allyloxycarbonyl,chloro- or bromoallyloxycarbonyl, alkenyloxy, chloro- or bromoalkenyloxy, alkynyloxy, benzoyloxy, alkoxy, phenyl, phenoxy, phenylalkoxy, alkyl- or dialkylaminocarbonyl,alkyl- or dialkylaminocarbonyloxy, phenylaminocarbonyl, phenylaminocarbonyloxy, phthalimidyl, saccharinyl-2, pyridyl or benzothiazolyl-2-mercapto;
alkoxyalkyl in which the alkoxy is monosubstituted by hydroxyl, chlorine, bromine, cyano, alkoxy, alkoxycarbonyl, alkoxycarbonyloxy or alkylcarbonyloxy;
β-hydroxy- or β-alkylcarbonyloxy- γ-propynyloxy- or γ-allyloxy-propyl;

alkenyl or alkenyl monosubstituted by phenyl, chlorine or bromine;
alkynyl;
($C_{5-7}$)cycloalkyl (preferably cyclohexyl) or ($C_{5-7}$)cycloalkyl (preferably cyclohexyl) substituted by up to three methyl groups; or
phenyl or phenyl substituted by up to three substituents independently selected from chlorine, bromine, methyl and ($C_{1-2}$)alkoxy, with the proviso that at least one of $R_3$ and $R_4$ is other than cycloalkyl, substituted cycloalkyl, phenyl or substituted phenyl and when $R_3$ is hydrogen, $R_4$ is other than hydrogen. The alkyl groups and alkoxy groups in substituents as $R_3$ and/or $R_4$ contain, unless otherwise stated, up to 4, preferably up to 2, carbon atoms, and the alkenyl and alkynyl groups 2 to 4, preferably 3 or 4, carbon atoms.

$R_5$ is hydrogen, chlorine, bromine, ($C_{1-2}$)alkyl, ($C_{1-2}$)alkoxy or phenoxy, and $R_6$ is hydrogen; ($C_{1-2}$)alkyl; ($C_{1-2}$)alkoxy; cyano; formylamino; alkylcarbonylamino in which the alkyl group is unsubstituted or monosubstituted by hydroxyl, chlorine, bromine, alkoxy, phenyl or phenoxy;
benzoylamino; alkenylcarbonylamino; aminocarbonylamino; alkylaminocarbonylamino; alkoxycarbonylamino in which the alkoxy group is unsubstituted or monosubstituted by alkoxy or phenyl;
($C_{1-2}$)alkyl- or phenylsulphonylamino; di-($C_{1-2}$)alkylaminosulphonylamino; chlorine; bromine or phenoxy, with the proviso that when $R_5$ is chlorine, bromine or phenoxy $R_6$ is other than chlorine, bromine or phenoxy, the alkyl and alkoxy moieties in substituents as $R_6$, unless otherwise stated, contain up to 4, preferably up to 2, carbon atoms and the alkenyl moieties contain 2 to 4, preferably 2 or 3, carbon atoms.

Preferably, each of $R_3$ and $R_4$, independently, is $R_3'$ and $R_4'$, where each of $R_3'$ and $R_4'$, independently is hydrogen, ($C_{1-4}$) alkyl or ($C_{1-4}$)alkyl monosubstituted by chlorine, hydroxyl, cyano, thiocyano, ($C_{1-2}$)alkylcarbonyl, formyloxy, alkyl($C_{1-2}$)carbonyloxy, chloroalkyl($C_{1-2}$)carbonyloxy, allyloxy, 3-chloro- or 3-bromoallyloxy,prop-2-ynyloxy, alkoxy($C_{1-2}$)carbonyl, benzoyloxy, alkoxy($C_{1-2}$)carbonyloxy, allyloxycarbonyl, chloroallyloxycarbonyl, methoxyethoxycarbonyl, phenylaminocarbonyloxy, ($C_{1-3}$)alkoxy, phenyl($C_{1-2}$)alkoxy, ($C_{1-2}$)alkoxycarbonyl($C_{1-2}$)alkoxy, chloroethoxy, cyano($C_{1-2}$)alkoxy or diethylaminocarbonyl;

β-hydroxy-or β-acetoxy-γ-prop-2-ynyloxypropyl; allyl; 2-methylallyl; 3-chloroallyl; 3-phenylallyl; prop-2-ynyl; cyclohexyl, phenyl or benzyl, with the proviso that at least one of $R_3'$ and $R_4'$ is other than cyclohexyl, phenyl or benzyl and when $R_3'$ is hydrogen, $R_4'$ is other than hydrogen.

More preferably, each of $R_3$ and $R_4$, independently, is $R_3''$ and $R_4''$, where each of $R_3''$ and $R_4''$, independently, is ($C_{2-4}$)alkyl or ($C_{2-4}$)alkyl monosubstituted by chlorine, hydroxyl, ($C_{1-2}$)alkoxy, cyano($C_{1-2}$)alkoxy, chloroethoxy, alkoxy($C_{1-2}$) carbonylethoxy, allyloxy, prop-2-ynyloxy, phenylmethoxy, cyano, alkyl($C_{1-2}$)carbonyloxy, alkoxy($C_{1-2}$)carbonyl or alkoxy($C_{1-2}$)carbonyloxy;
benzyl; allyl; 2-methylallyl;
3-chloroallyl; 3-phenylallyl or prop-2-ynyl; provided that $R_3''$ and $R_4''$ cannot both be benzyl.

Most preferably each of $R_3$ and $R_4$, independently, is $R_3'''$ and $R_4'''$, where each of $R_3'''$ and $R_4'''$, independently, is acetoxyethyl, allyloxyethyl,prop-2-ynyloxyethyl,β-acetoxypropyl, allyl, 2-methylallyl or phenylmethoxyethyl.

$R_5$ is preferably $R_5'$, where $R_5'$ is hydrogen, chlorine, methyl or ($C_{1-2}$)alkoxy. Most preferably $R_5$ is $R_5''$, where $R_5''$ is hydrogen or ($C_{1-2}$)alkoxy, with hydrogen being especially preferred.

$R_6$ is preferably $R_6'$, where $R_6'$ is hydrogen, methyl, alkyl($C_{1-2}$)carbonylamino, chloroalkyl($C_{1-2}$)carbonylamino, benzoylamino,alkoxy($C_{1-2}$)carbonylamino,alkoxy($C_{1-2}$)ethoxycarbonylamino, methylsulphonylamino, dimethylaminosulphonylamino, crotonoylamino, aminocarbonylamino or ethylaminocarbonylamino. More preferably $R_6$ is $R_6''$, where $R_6''$ is hydrogen, methyl or alkyl($C_{1-2}$)carbonylamino, with acetylamino being especially preferred.

Thus, more preferred compounds of formula I are those wherein $R_1$ is $R_1'$, $R_2$ is $R_2'$ and K is K', especially those wherein $R_3$ is $R_3'$, $R_4$ is $R_4'$, $R_5$ is $R_5'$ and $R_6$ is $R_6'$.

Of these, those where $R_1$ is $R_1''$, $R_2$ is $R_2''$, $R_3$ is $R_3''$, $R_4$ is $R_4''$, $R_5$ is $R_5''$ and $R_6$ is $R_6''$ are even more preferred, especially those wherein $R_1$ is $R_1'''$, $R_2$ is $R_2'''$, $R_3$ is $R_3'''$ and $R_4$ is $R_4'''$, with those compounds wherein $R_1$ is benzyl or mono- or dichlorobenzyl, $R_2$ is cyano, each of $R_3$ and $R_4$, independently, is acetoxyethyl, allyloxyethyl, β-acetoxypropyl, allyl or 2-methylallyl, $R_5$ is hydrogen and $R_6$ is acetylamino being most preferred. Also preferred are the compounds of Formula I wherein $R_1$ is benzyl, chlorobenzyl or dichlorobenzyl, $R_2$ is cyano, $R_3$ and $R_4$ are independently $R_3''$ and $R_4''$, with the proviso that at least one of them is other than benzyl, $R_5$ is hydrogen, and $R_6$ is acetamido. In the compounds of formula I and the preferred subclasses of such compounds preferably $R_1$ is bound to the 1-position of the triazole ring.

The present invention also provides a process for the production of compounds of formula I comprising coupling the diazotized amine of formula II,

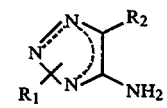

with a compound of formula III,

H-K     III

The coupling reaction as well as the diazotization of the amine of formula III may be carried out in accordance with known methods.

The compounds of formula II are either known or may be prepared in analogy with known methods. For example, those compounds wherein $R_1$ is in the 1-position of the triazole ring may be prepared in analogy with the procedures described by R. E. Hoover et al, J. Am. Chem. Soc. 78, 5832 (1956) and A. Albert, J. Chem. Soc. (C) 1970, 230. Those in which $R_1$ is in the 2-position may be prepared by nitrosating malononitrile and condensing the same with para-toluenesulphonic acid chloride to yield a compound of formula IV,

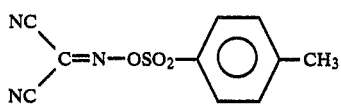

followed by treating the compound of formula IV with the corresponding R₁-substituted hydrazine with ring formation (e.g. with ethanol at the boil) to give the desired aminotriazole.2-Phenyldiazonium asubstituted phenyldiazonium chloride with malonic acid dinitrile, reaction with hydroxylaminochlorohydrate, condensation with para-toluenesulphonic acid chloride and acidification, preferably with concentrated hydrochloric acid, whereby ring closure by the splitting off of para-toluenesulfonic acid occurs to yield the desired aminotriazole.

The compounds of formula III are known or may be prepared in accordance with known methods from available starting materials.

The compounds of formula I are useful as disperse dyes for exhaust dyeing, pad dyeing or printing, from aqueous suspensions, textile substrates consisting of or comprising synthetic or semi-synthetic, hydrophobic, high molecular weight organic materials. Preferred substrates are those which consist of or comprise linear, aromatic polyesters, cellulose-2½-acetate, cellulose triacetate or synthetic polyamides.

The dyestuffs of the invention display good build-up and exhaust upon the above substrates and give dyeings having notable fastness properties, for example fastness to light, washing, rubbing, permanent-press finishing, sublimation, dry cleaning and sea water.

The compounds of formula I may be made up into dyeing preparations in accordance with known methods, for example by grinding in the presence of dispersing agents and/or fillers with optional drying in vacuo or spray drying. After the addition of water, the preparations can be used for dyeing from a long or short bath.

Dyeing and printing may be carried out in accordance with known methods, for examples as described in French Pat. No. 1,445,371.

The following Examples further serve to illustrate the invention. In the Examples all parts are by weight and all temperatures in degrees centigrade.

EXAMPLE 1

Preparation of the dyestuff of the formula

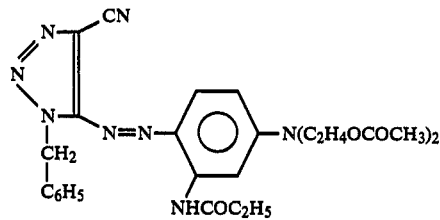

20 Parts of 5-amino-1-benzyl-4-cyano-1,2,3-triazole are slowly added at 0°–5° to a mixture of 107 parts nitrosylsulphuric acid (prepared by dissolving 7 parts sodium nitrite in 100 parts concentrated sulphuric acid), 85 parts glacial acetic acid and 15 parts propionic acid. The mixture obtained is mixed at 0°–5° with a mixture of 85 parts glacial acetic acid and 15 parts propionic acid and the whole is stirred at 0°–5° for 3 hours. Subsequently, a solution of 34 parts 1-propionylamino-3-(N,N-di-β-acetoxyethyl)aminobenzene in 85 parts glacial acetic acid and 15 parts propionic acid is added dropwise thereto and the resulting mixture is stirred for 3 hours at 0°–5°. The reaction mixture is then poured, with stirring, onto a 600 parts ice and 300 parts water mixture whereby the dyestuff precipitates. The dye is filtered, washed free of acid and salt with water and dried. The dyestuff obtained dyes synthetic fibres in red shades.

Preparation of 5-amino-1-benzyl-4-cyano-1,2,3-triazole 13.3 Parts benzylazide are added dropwise at room temperature to a suspension of 6.8 parts sodium ethoxide and 8.4 parts cyanoacetamide in 250 parts absolute alcohol. After the addition is complete the reaction mixture is stirred for 1½ hours at boiling temperature, cooled to room temperature, filtered, washed with water and dried in a vacuum.

11 Parts of the 5-amino-1-benzyl-4-carbamoyl-1,2,3-triazole obtained are suspended in 50 parts dimethylformamide. At 0°, 15.3 parts phosphorus oxychloride are added dropwise thereto and the mixture is stirred for 15 minutes at room temperature and 15 minutes at 80°. After cooling to 25°, 50 parts 1 N hydrochloric acid are added thereto and the whole is heated to 100° for approximately 5 minutes. On cooling to room temperature the desired product precipitates which is then filtered and dried.

Further dyes according to the present invention, which may be prepared in analogy with the procedure described in Example 1, are given in the following Table 1. The dye shade on polyester is also indicated.

TABLE 1

The dyes are of the general formula

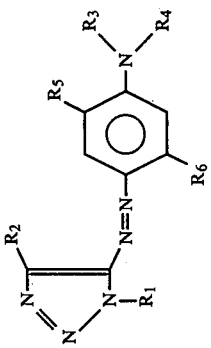

| Example No. | $R_1$ | $R_2$ | $R_3$ | $R_4$ | $R_5$ | $R_6$ | Shade on polyester fibers |
|---|---|---|---|---|---|---|---|
| 2 | —CH$_2$—C$_6$H$_5$ | —CN | —C$_2$H$_4$OCOCH$_3$ | —C$_2$H$_4$OCOCH$_3$ | H | —NHCOCH$_3$ | red |
| 3 | " | " | " | —C$_2$H$_5$ | H | " | scarlet |
| 4 | " | " | —CH$_2$CH=CHCl | —C$_2$H$_4$OCOCH$_3$ | H | —NHCOC$_2$H$_5$ | red |
| 5 | —C$_6$H$_5$ | " | —C$_2$H$_4$OCOCH$_3$ | —C$_2$H$_4$CN | H | —NHCOCH$_3$ | " |
| 6 | " | " | —CH$_2$CH=CHCl | —C$_2$H$_4$OCOCH$_3$ | H | " | " |
| 7 | " | " | —C$_2$H$_4$OCOCH$_3$ | " | H | " | " |
| 8 | —CH$_2$—(2,4-Cl$_2$C$_6$H$_3$) | " | " | —C$_2$H$_4$OCOCH$_3$ | H | —NHCOCH$_3$ | " |
| 9 | " | " | " | " | H | —NHCOCH$_3$ | " |
| 10 | —CH$_2$—(4-ClC$_6$H$_4$) | " | " | " | H | —NHCOC$_2$H$_5$ | " |
| 11 | —C$_6$H$_5$ | —CO$_2$CH$_3$ | " | " | —OC$_2$H$_5$ | —NHCOCH$_3$ | " |
| 12 | —CH$_2$—C$_6$H$_5$ | —CO$_2$C$_2$H$_5$ | —C$_2$H$_4$CO$_2$C$_2$H$_5$ | —C$_2$H$_4$CO$_2$C$_2$H$_5$ | H | —NHCOCH$_3$ | " |
| 13 | —C$_6$H$_5$ | —CN | " | —C$_2$H$_4$OCOCH$_3$ | H | —NHCOCH$_3$ | " |
| 14 | " | " | —C$_2$H$_4$OCOCH$_3$ | —C$_2$H$_4$OCOCH$_3$ | H | " | " |
| 15 | —CH$_2$—(4-ClC$_6$H$_4$) | " | " | " | H | " | " |
| 16 | " | " | " | " | H | " | " |
| 17 | —CH$_2$—C$_6$H$_5$ | " | —C$_2$H$_4$OCOCH$_3$ | —C$_2$H$_4$OCOCH$_3$ | H | " | " |
| 18 | —C$_6$H$_5$ | " | —CH$_2$CH=CHCl | —CH$_2$CH=CHCl | H | —NHCOCH$_3$ | " |
| 19 | " | " | " | —C$_2$H$_4$CN | H | —CH$_3$ | scarlet |
| 20 | " | " | " | " | H | —NHCOCH$_3$ | red |
| 21 | —CH$_2$—C$_6$H$_5$ | " | " | —CH$_2$CH=CH$_2$ | H | " | " |
| 22 | " | " | —CH$_2$CH=CH$_2$ | " | H | " | " |

TABLE 1-continued

The dyes are of the general formula $$\begin{array}{c} R_2 \\ \diagup \\ N \diagdown \diagup \diagdown \\ \| \quad \| \\ N \diagdown \diagup N \diagdown R_1 \end{array} - N=N - \begin{array}{c} R_5 \\ \diagdown \\ \diagdown \diagdown \diagup \diagdown \\ \diagdown \diagdown \diagdown \diagup \end{array} - N \begin{array}{c} R_3 \\ \diagdown \\ R_4 \end{array}$$

| Example No. | $R_1$ | $R_2$ | $R_3$ | $R_4$ | $R_5$ | $R_6$ | Shade on polyester fibers |
|---|---|---|---|---|---|---|---|
| 23 | —$C_6H_5$ | " | —$C_2H_4Cl$ | —$C_2H_4Cl$ | H | " | violet |
| 24 | " | " | —$C_2H_4OCOCH_3$ | —$C_2H_4OCOCH_3$ | —$OC_2H_5$ | " | scarlet |
| 25 | —$CH_2C_6H_5$ | " | " | —$C_2H_4CN$ | H | H | orange |
| 26 | —$C_6H_4$—m-$CH_3$ | " | " | " | H | H | red |
| 27 | —$C_6H_4$—p-$CH_3$ | —$CO_2CH_3$ | " | " | H | —NH—COCH_3 | " |
| 28 | —$C_6H_5$ | " | " | —$C_2H_4OCOCH_3$ | H | " | scarlet |
| 29 | —$CH_2C_6H_5$ | —CN | —$CH_2CH=CHCl$ | " | H | " | orange |
| 30 | " | " | —$C_2H_4OCONHC_6H_5$ | " | H | —NHCOCH_3 | red |
| 31 | —$C_6H_5$ | " | —$C_2H_4OCOC_6H_5$ | —$C_2H_5$ | H | " | " |
| 32 | —$CH_2C_6H_5$ | " | —$C_2H_5$ | —$C_6H_5$ | H | —NHCOCH_3 | rubine |
| 33 | " | " | —$C_2H_4CN$ | —$CH_2C_6H_5$ | H | " | red |
| 34 | —$C_6H_5$ | " | —$CH_2CH=CHCl$ | —$C_2H_4OCOCH_2CH_2Cl$ | H | " | " |
| 35 | —$CH_2C_6H_5$ | " | —$C_2H_4CN$ | —$C_2H_4OCOCH_3$ | H | " | " |
| 36 | —$C_6H_5$ | " | —$C_2H_4OCOCH_3$ | " | H | —NHCOCH_2CH_2Cl | " |
| 37 | " | " | " | —$CH_2CH=CH_2$ | H | —NHCOCHCH_3 \\ Cl | " |
| 38 | | | | | | | |
| 39 | | | | | | | |
| 40 | " | " | " | —$C_2H_4OCOCH_3$ | H | —NHSO_2CH_3 | " |
| 41 | —$CH_2$—⌬—Cl | " | " | —$C_2H_4SCN$ | H | —NHCOC_6H_5 | " |
| 42 | " | " | " | " | H | —NHCOCH_3 | " |
| 43 | —$C_6H_5$ | " | —$C_2H_4SCN$ | " | | | |
| 44 | " | " | —$C_2H_5$ | —$C_2H_4$—S—⟨benzothiazolyl⟩ | H | " | rubine |
| 45 | —$CH_2C_6H_5$ | " | " | —$C_2H_4$—N⟨phthalimide⟩ | H | " | red |
| 46 | —$C_6H_5$ | " | —$C_2H_4OCOCH_3$ | —$C_2H_4OCOCH_3$ | H | —NHCO_2CH_3 | " |

TABLE 1-continued

The dyes are of the general formula $$\begin{array}{c} R_2 \\ N{=}N \end{array} \text{(pyrazole)} {-} N{=}N{-} \text{(phenyl with } R_5, R_6\text{)} {-} N(R_3)(R_4)$$

| Example No. | $R_1$ | $R_2$ | $R_3$ | $R_4$ | $R_5$ | $R_6$ | Shade on polyester fibers |
|---|---|---|---|---|---|---|---|
| 47 | " | " | —C$_2$H$_4$CN | " | H | —NHCOOC$_2$H$_4$OCH$_3$ | " |
| 48 | " | " | —C$_2$H$_4$OCOCH$_3$ | " | —CH$_3$ | —NHCOCH$_3$ | " |
| 49 | " | " | " | " | —Cl | " | " |
| 50 | —CH$_2$C$_6$H$_5$ | " | —CH$_2$C(CH$_3$)=CH$_2$ | —CH$_2$CH=CH$_2$ | H | " | " |
| 51 | (2-Cl-benzyl) —CH$_2$— | " | " | " | H | " | " |
| 52 | —C$_6$H$_5$ | " | " | " | H | " | " |
| 53 | (2,4-diCl-benzyl) —CH$_2$— | " | " | " | H | " | " |
| 54 | " | " | —CH$_2$CH=CH$_2$ | —CH$_2$CH=CH$_2$ | H | " | " |
| 55 | (2-Cl-benzyl) —CH$_2$— | " | —CH$_2$C(CH$_3$)=CH$_2$ | —CH$_2$C(CH$_3$)=CH$_2$ | H | " | " |
| 56 | —CH$_2$C$_6$H$_5$ | " | —CH$_2$C$_6$H$_5$ | —CH$_2$C$_6$H$_5$ | H | —NHCONH$_2$ | " |
| 57 | " | " | —CH$_2$C(CH$_3$)=CH$_2$ | —CH$_2$C(CH$_3$)=CH$_2$ | H | —NHCONHC$_2$H$_5$ | " |
| 58 | " | " | —CH$_2$CH=CH$_2$ | —CH$_2$CH=CH$_2$ | H | —NHCOOC$_2$H$_4$OCH$_3$ | " |
| 59 | " | —CONH$_2$ | —C$_2$H$_4$OCOCH$_3$ | —C$_2$H$_4$OCOCH$_3$ | —OC$_2$H$_5$ | —NHCOCH$_3$ | " |
| 60 | " | —CN | —C$_2$H$_4$OH | —C$_2$H$_4$CN | H | " | rubine red |
| 61 | " | " | | | | | |

TABLE 1-continued

The dyes are of the general formula

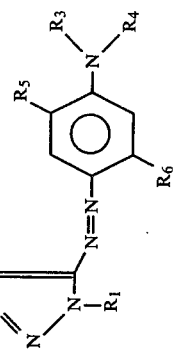

| Example No. | $R_1$ | $R_2$ | $R_3$ | $R_4$ | $R_5$ | $R_6$ | Shade on polyester fibers |
|---|---|---|---|---|---|---|---|
| 62 | " | " | " | $-C_2H_4OH$ | H | $-NHCOC_2H_5$ | " |
| 63 | " | $-CONH_2$ | " | $-C_2H_4OCOCH_3$ | H | " | " |
| 64 | " | $-CN$ | " | $-C_2H_4OH$ | H | " | " |
| 65 | " | " | $-C_2H_4OCH_2CO_2CH_3$ | $-C_2H_4OCH_2CO_2CH_3$ | H | " | " |
| 66 | " | " | $-C_2H_4OCH_2CN$ | $-C_2H_4OCH_2CN$ | H | $-NH-COC_2H_5$ | " |
| 67 | " | " | $-CH_2CH(CH_3)OCOCH_3$ | $-CH_2CH(CH_3)OCOCH_3$ | H | " | " |
| 68 | " | " | $-C_2H_4OCH_2CH_2CN$ | $-C_2H_4OCH_2CH_2CN$ | H | " | " |
| 69 | " | " | $-C_2H_4OC_2H_4CO_2CH_3$ | $-C_2H_4OC_2H_4CO_2CH_3$ | H | " | " |
| 70 | " | " | $-C_2H_4OC_2H_4Cl$ | $-C_2H_4OC_2H_4Cl$ | H | " | " |
| 71 | " | " | $-C_2H_4OCOCH_3$ | $-C_2H_4OCOCH_3$ | H | $-NHCOCH-CH_3$ $\|$ $OH$ | " |
| 72 | " | " | $-CH_2CH=CH_2$ | $-CH_2CH=CH_2$ | H | " | orange |
| 73 | " | " | $-C_2H_4CN$ | $-CH_2C\equiv CH$ | H | $-NHCOCH=CHCH_3$ | " |
| 74 | " | " | $-CH_2COOC_2H_5$ | $-CH_2COOC_2H_5$ | H | $-NHCOCH_3$ | red |
| 75 | " | " | $-C_2H_4CON(C_2H_5)_2$ | $-C_2H_5$ | H | " | " |
| 76 | " | " | $-C_2H_4OCHO$ | " | H | " | " |
| 77 | " | " | $-CH_2CH=CHC_6H_5$ | $-CH_2CH=CHC_6H_5$ | H | " | scarlet |
| 78 | " | " | $-C_6H_{11}$ | $-C_2H_4CN$ | H | | |
| 79 | " | " | $-C_6H_5$ | " | H | H | |
| 80 | " | " | | | | | |
| 81 | " | " | $-CH_2CH-OCOCH_3$ $\|$ $CH_3$ | $-CH_2CH-O-COCH_3$ $\|$ $CH_3$ | H | $-NHCOCH_3$ | red |
| 82 | " | " | n-$C_4H_8OCOCH_3$ | n-$C_4H_8OCOCH_3$ | H | " | " |
| 83 | " | " | n-$C_3H_6OCOCH_3$ | n-$C_3H_6OCOCH_3$ | H | " | " |
| 84 | " | " | n-$C_4H_8CN$ | n-$C_4H_8CN$ | H | " | " |
| 85 | " | " | n-$C_3H_6CN$ | n-$C_3H_6CN$ | H | " | " |
| 86 | " | $-COCH_3$ | $-C_2H_4OCOCH_3$ | $-C_2H_4COCH_3$ | H | $-NHCOCH_3$ | orange |
| 87 | " | $-COOH$ | " | " | H | " | red |
| 88 | " | $-NO_2$ | " | " | H | " | scarlet |
| 89 | " | $-SO_2CH_3$ | " | " | H | " | red |
| 90 | $-CH_2CO_2C_2H_5$ | $-CN$ | " | " | H | " | " |
| 91 | $-CH_2CN$ | " | " | " | H | " | " |
| 92 | H | " | " | " | H | " | " |
| 93 | $-CH_2CONH_2$ | " | " | " | H | " | " |

TABLE 1-continued

The dyes are of the general formula $$\text{pyrazole-N=N-}\underset{R_6}{\underset{|}{\bigcirc}}\text{-N}\underset{R_4}{\overset{R_3}{<}}\quad\text{with } R_1, R_2, R_5$$

| Example No. | R₁ | R₂ | R₃ | R₄ | R₅ | R₆ | Shade on polyester fibers |
|---|---|---|---|---|---|---|---|
| 94 | —CH₂CH₂CN | " | " | " | " | " | " |
| 95 | —CH₂CH₂CO₂CH₃ | " | " | " | " | " | " |
| 96 | —CH₂CH₂OCOCH₃ | " | " | " | " | " | " |
| 97 | —CH₂COC₆H₅ | " | " | " | " | " | " |
| 98 | —CH₂CH₂Cl | " | " | " | " | " | " |
| 99 | —CH₂CH=CHCl | " | " | " | " | " | " |
| 100 | —CH₂CH=CHC₆H₅ | " | " | " | " | " | " |
| 101 | —CH₂C₆H₅ | " | —C₂H₄OCOC₂H₅ | —C₂H₄OCOC₂H₅ | H | H | scarlet |
| 102 | " | " | —C₂H₄CO₂CH₃ | —C₂H₄CO₂CH₃ | H | —NHCOC₂H₅ | red |
| 103 | " | " | —C₂H₄OCHO | —C₂H₄OCHO | H | " | " |
| 104 | " | " | —CH₂CO₂CH₃ | —CH₂CO₂CH₃ | H | —NHCOCH₃ | " |
| 105 | " | " | —CH₂CO₂C₂H₅ | —CH₂CO₂C₂H₅ | H | " | " |
| 106 | " | " | —CH₂CH=CH₂ | —CH₂CH=CH₂ | H | —CH₃ | " |
| 107 | " | " | " | " | H | H | scarlet |
| 108 | " | " | —C₂H₅ | —C₂H₄CN | H | —CH₃ | rubine |
| 109 | " | " | —C₂H₄OCOCH₃ | —C₂H₄OCOCH₃ | OCH₃ | —NHCOCH₃ | red |
| 110 | " | " | " | " | H | —NHCO₂C₂H₄OC₂H₅ | " |
| 111 | " | " | " | " | H | —NHCOCH₂Cl | " |
| 112 | " | " | " | " | H | —NH—COCH₃ | " |
| 113 | " | " | —C₂H₄CO₂CH₂CH=CH₂ | —C₂H₄CO₂CH₂CH=CH₂ | H | " | " |
| 114 | " | " | —C₂H₄CO₂CH₂CH=CHCl | —C₂H₄CO₂CH₂CH=CHCl | " | " | " |
| 115 | " | " | —CH₂CH(OH)CH₂—O—CH₂—C≡CH | H | H | " | " |
| 116 | " | " | —CH₂CH(OCOCH₃)—CH₂—OCH₂—C≡CH | H | H | " | " |
| 117 | —CH₂C≡CH | " | —CH₂C≡CH | —CH₂C≡CH | H | H | orange |
| 118 | " | " | —C₆H₅ | H | H | —NHCOC₂H₅ | red |
| 119 | " | " | —C₂H₄OC₂H₅ | —C₂H₄OC₂H₅ | H | " | " |
| 120 | " | " | —C₂H₄OC₃H₇n | —C₂H₄OC₃H₇n | H | " | " |
| 121 | " | " | —C₂H₄OCH₃ | —C₂H₄OCH₃ | H | " | " |
| 122 | " | " | —C₂H₄CO₂C₂H₄OCH₃ | —C₂H₄CO₂C₂H₄OCH₃ | H | —NHCOCH₃ | " |
| 123 | " | " | —C₂H₄OCOCH₃ | —C₂H₄OCOCH₃ | H | —NHSO₂N(CH₃)₂ | " |
| 124 | " | " | —C₂H₄OCO₂C₂H₅ | —C₂H₄OCO₂C₂H₅ | H | —NHCOCH₃ | " |
| 125 | " | " | —CH₂CH=CHCl | —CH₂CH=CHCl | —OC₂H₅ | " | " |

TABLE 1-continued

The dyes are of the general formula (structure: pyrazole ring with R1 on N, R2 substituent, connected via —N=N— to a benzene ring bearing R5, R6 and —N(R3)(R4))

| Example No. | R1 | R2 | R3 | R4 | R5 | R6 | Shade on polyester fibers |
|---|---|---|---|---|---|---|---|
| 126 | " | " | —CH$_2$C≡CH | —CH$_2$C≡CH | H | —NHCOOCH$_3$ | " |
| 127 | " | " | —CH$_2$CH$_2$OCOCH$_3$ | —CH$_2$CH$_2$OCOCH$_3$ | H | —NHCOOC$_2$H$_5$ | " |
| 128 | " | " | —CH$_2$CH$_2$OCOC$_2$H$_5$ | —CH$_2$CH$_2$OCOC$_2$H$_5$ | H | —NHCOCH$_3$ | " |
| 129 | 2-chloro-6-methylphenyl | " | —CH$_2$CH$_2$OCOCH$_3$ | —CH$_2$CH$_2$OCOCH$_3$ | H | " | " |
| 130 | 4-chlorophenyl | " | " | " | " | " | " |
| 131 | " | " | —CH$_2$—C(CH$_3$)=CH$_2$ | —CH$_2$—C(CH$_3$)=CH$_2$ | H | " | " |
| 132 | —CH$_2$C$_6$H$_5$ | " | —CH$_2$CH$_2$CN | —CH$_2$CH$_2$OCOCH$_3$ | —OC$_2$H$_5$ | —CH$_3$ | " |
| 133 | " | " | " | —CH$_2$—C≡CH | " | H | " |
| 134 | " | " | " | —CH$_2$CH=CHCl | " | —NHCOCH$_3$ | " |
| 135 | " | " | —C$_2$H$_5$ | —CH$_2$CH=CH$_2$ | H | " | " |
| 136 | " | " | " | —C$_2$H$_4$OCONHC$_6$H$_5$ | " | " | " |
| 137 | " | " | " | " | " | " | " |
| 138 | " | " | " | —C$_2$H$_4$—O—C$_6$H$_5$ | " | " | " |
| 139 | " | " | " | —C$_2$H$_4$CN | " | " | " |
| 140 | " | " | " | —CH$_2$C≡CH | " | " | " |
| 141 | " | " | " | —CH$_2$CH=CHCl | " | " | " |
| 142 | " | " | " | —CH$_2$CH=CH$_2$ | " | " | " |
| 143 | " | " | " | —CH$_2$C$_6$H$_5$ | " | " | " |
| 144 | " | " | " | —C$_2$H$_4$OCOCH$_3$ | " | " | " |
| 145 | " | " | " | —C$_2$H$_4$OCONHC$_2$H$_5$ | " | " | " |
| 146 | " | " | " | —CH$_2$CO$_2$C$_2$H$_5$ | " | " | " |
| 147 | " | " | " | —C$_2$H$_4$CO$_2$CH$_3$ | " | " | " |
| 148 | " | " | " | —C$_2$H$_4$OCO$_2$CH$_3$ | " | " | " |
| 149 | " | " | —C$_2$H$_4$OCH$_2$CH=CH$_2$ | —C$_2$H$_4$OCH$_2$CH=CH$_2$ | " | " | " |
| 150 | —CH$_2$-(4-chlorophenyl) | " | " | " | " | " | " |

TABLE 1-continued

The dyes are of the general formula

[Structure: pyrazole-azo-phenyl diamine with substituents R1-R6]

| Example No. | R$_1$ | R$_2$ | R$_3$ | R$_4$ | R$_5$ | R$_6$ | Shade on polyester fibers |
|---|---|---|---|---|---|---|---|
| 151 | -CH$_2$-C$_6$H$_3$(Cl)(Cl) | " | " | " | " | " | " |
| 152 | " | " | -C$_2$H$_4$OCH$_2$CH=CHCl | -C$_2$H$_4$OCH$_2$CH=CHCl | " | " | " |
| 153 | " | " | -C$_2$H$_4$OCH$_2$-C$_6$H$_5$ | -C$_2$H$_4$OCH$_2$C$_6$H$_5$ | " | " | " |
| 154 | " | " | " | -C$_2$H$_4$OCH$_2$CH=CH$_2$ | " | " | " |
| 155 | " | " | -C$_2$H$_5$ | " | " | " | " |
| 156 | " | " | -C$_2$H$_4$OCH$_2$CH=CH$_2$ | " | " | " | scarlet |
| 157 | " | " | " | " | " | H | red |
| 158 | " | " | -C$_2$H$_4$OCH$_2$C$_6$H$_5$ | -C$_2$H$_4$OCH$_2$CH=CH$_2$ | " | -CH$_3$ | " |
| 159 | " | " | -C$_2$H$_5$ | -C$_2$H$_4$OCH$_2$C$_6$H$_5$ | " | -NHCOCH$_3$ | " |
| 160 | " | " | " | " | " | -CH$_3$ | " |
| 161 | " | " | " | " | " | -NHCOCH$_3$ | " |
| 162 | " | " | " | " | H | H | " |
| 163 | -CH$_2$C$_6$H$_4$-p-Cl | " | -C$_2$H$_4$OCH$_2$C≡CH | -C$_2$H$_4$OCH$_2$CH=CH$_2$ | H | -CH$_3$ | scarlet |
| 164 | -CH$_2$C$_6$H$_5$ | " | " | -C$_2$H$_4$OCH$_2$C≡CH | H | -NHCOCH$_3$ | red |
| 165 | " | " | -C$_2$H$_4$OCOCH$_3$ | " | " | -CH$_3$ | " |
| 166 | " | " | -C$_2$H$_5$ | " | " | -NHCOCH$_3$ | " |
| 167 | " | " | -C$_2$H$_4$CN | " | " | -CH$_3$ | " |
| 168 | " | " | " | " | " | -NHCOCH$_3$ | " |
| 169 | " | " | " | " | " | " | " |
| 170 | " | " | " | -C$_2$H$_4$OCH$_2$CH=CH$_2$ | " | " | " |
| 171 | " | " | " | -C$_2$H$_4$OCH$_2$C$_6$H$_5$ | " | -CH$_3$ | orange |
| 172 | " | " | " | -C$_2$H$_4$OCH$_2$CH=CH$_2$ | " | H | " |
| 173 | " | " | " | " | " | -NHCOCH$_3$ | red |
| 174 | " | " | " | " | " | -CH$_3$ | scarlet |
| 175 | " | " | -C$_2$H$_4$OCOCH$_3$ | " | " | -NHCOCH$_3$ | red |
| 176 | " | " | -C$_2$H$_4$CO$_2$C$_2$H$_5$ | " | " | -CH$_3$ | scarlet |
| 177 | " | " | " | " | " | -NHCOCH$_3$ | scarlet |
| 178 | " | " | " | " | " | -CH$_3$ | red |
| 179 | " | " | " | -C$_2$H$_4$OCH$_2$C$_6$H$_5$ | " | -NHCOCH$_3$ | " |
| 180 | " | " | -C$_2$H$_4$OCOCH$_3$ | " | " | -NHCOCH$_3$ | " |
| 181 | " | " | " | " | " | " | " |
| 182 | " | " | " | " | " | -CH$_3$ | scarlet |

TABLE 1-continued

The dyes are of the general formula

R1—[triazole ring with R2]—N=N—[benzene ring with R5, R6]—N(R3)(R4)

| Example No. | R1 | R2 | R3 | R4 | R5 | R6 | Shade on polyester fibers |
|---|---|---|---|---|---|---|---|
| 183 | —CH2—C6H4—Cl | " | —CH2CH=CH2 | —CH2CH=CH2 | " | —NHCOCH3 | red |
| 184 | " | " | —C2H4OCH2C6H5 | —C2H4OCH2C6H5 | " | " | red |
| 185 | —CH2C6H5 | —SCN | " | —C2H4OCH2CH=CH2 | " | " | " |

EXAMPLE 186:

Preparation of the dyestuff of the formula

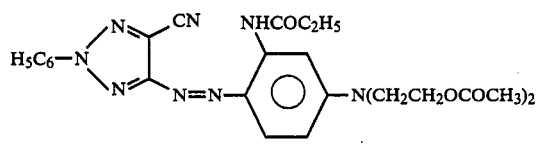

18.5 Parts 2-phenyl-4-cyano-5-amino-1,2,3-triazole are diazotized and coupled with 34 parts 1-propionylamino-3,N,N-(di-β-acetoxyethyl)aminobenzene in analogy with the procedure described in Example 1 and the dye obtained is isolated as described in Example 1.

Preparation of 2-phenyl-4-cyano-5-amino-1,2,3-triazole

20 Parts phenylazo-malonic dinitrile prepared by coupling phenyldiazonium chloride with malononitrile and 12.5 parts hydroxylaminochlorohydrate are suspended in 100 parts pyridine. 33.7 parts para-toluenesulfonic acid chloride are added thereto with ice cooling and stirred at room temperature from 5 hours. Then the mixture is adjusted with concentrated hydrochloric acid, extracted with 100 parts methylene chloride and the organic phase dried with the solvent being separated by distillation. The aminotriazole product is recrystallized from a methanol/water mixture.

In the following Table 2, further dyestuffs of the invention, which may be prepared in analogy with the procedure of Example 183, are given.

TABLE 2

The dyes corresponding to the general formula:

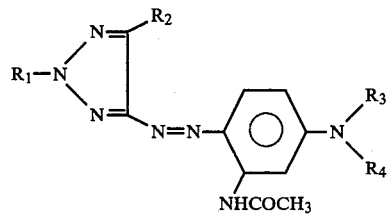

| Example No. | $R_1$ | $R_2$ | $R_3$ | $R_4$ | Shade on polyester |
|---|---|---|---|---|---|
| 187 | —$C_6H_5$ | —CN | —$C_2H_4OCOCH_3$ | —$C_2H_4OCOCH_3$ | red |
| 188 | " | " | " | —$C_2H_4CN$ | " |
| 189 | " | " | —$CH_2CH$=$CHCl$ | " | " |
| 190 | 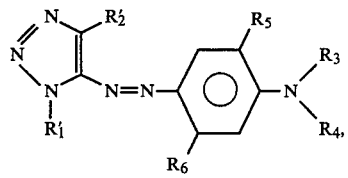 | " | " | " | " |
| 191 | (phenyl-Cl) | " | —$C_2H_4OCOCH_3$ | —$C_2H_4OCOCH_3$ | " |
| 192 | —$CH_3$ | " | " | " | " |

Application Example

7 Parts of the dyestuff of Example 1 are ground for 48 hours to a fine powder in a ball mill with 4 parts sodium dinaphthylmethanedisulphonate, 4 parts sodium acetylsulphate and 5 parts of anhydrous sodium sulphate.

1 Part of the so obtained dyestuff preparation is made into a paste with a little water and the suspension is added through a sieve to a dyebath of 4000 parts water containing 3 parts sodium laurylsulfate. 100 Parts of scoured polyester fibres are added to the bath (liquor ratio 1:40) at 40°–50° C. and then 20 parts of chlorinated benzene emulsified in water are added. The bath is heated slowly to 100° and dyeing is conducted for 1 to 2 hours at 95°–100°. The red dyed fibres are washed in water, soaped, washed again and dried. An even dyeing is obtained.

The dyes of Examples 2 to 192 may be employed in analogy with the above procedure for dyeing polyester fibres.

What is claimed is:

1. A compound of the formula wherein
$R_1'$ is hydrogen; $C_{1-4}$alkyl; $C_{1-4}$alkyl monosubstituted by fluoro, bromo, chloro, hydroxy, ($C_{1-4}$alkyl)carbonyl, $C_{1-4}$alkoxy, cyano, thiocyano, phenoxy, ($C_{1-4}$alkoxy)carbonyl, phenoxycarbonyl, ($C_{1-4}$alkoxy)ethoxycarbonyl, carbamoyl, ($C_{1-4}$alkyl)carbamoyl, di-($C_{1-4}$alkyl)carbamoyl, phenylcarbamoyl, N-$C_{1-4}$alkyl-N-phenylcarbamoyl, benzoyl, ($C_{1-4}$alkyl)carbonyloxy, phenylsulfonyl, $C_{1-4}$alkyl-sulfonyl, sulfamoyl, $C_{1-4}$alkylsulfamoyl, di-$C_{1-4}$alkylsulfamoyl, phenylsulfamoyl, N-$C_{1-4}$alkyl-N-phenylsulfamoyl, phenyl or substituted phenyl having 1 or 2 substituents each of which is independently chloro, bromo, nitro, cyano, trifluoromethyl, $C_{1-4}$alkyl or $C_{1-4}$alkoxy; $C_{2-4}$alkenyl; $C_{2-4}$alkenyl monosubstituted by chloro, bromo or phenyl; phenyl or substituted phenyl having 1 to 3 substituents each of which is independently $C_{1-4}$alkyl, $C_{1-4}$alkoxy, chloro, bromo, nitro, cyano (maximum of two), trifluoromethyl (maximum of two), ($C_{1-4}$alkoxy)carbonyl (maximum of two), formyl (maximum of one), ($C_{1-4}$alkyl)carbonyl (maximum of one), carbamoyl (maximum of one), ($C_{1-4}$alkyl)carbamoyl (maximum of one), di-($C_{1-4}$alkyl)carbamoyl (maximum of one), $C_{1-4}$alkylsulfonyl (maximum of one), phenylsulfonyl (maximum of one), sulfamoyl (maximum of one), $C_{1-4}$alkylsulfamoyl (maximum of one), di-$C_{1-4}$alkylsulfamoyl (maximum of one) or phenylsulfamoyl (maximum of one), $R_2'$ is cyano, thiocyano, nitro, —COOM, ($C_{1-4}$alkyl)carbonyl, benzoyl, ($C_{1-4}$alkoxy)carbonyl, ($C_{1-4}$alkoxy)ethoxycarbonyl, phenoxycarbonyl, carbamoyl, ($C_{1-4}$alkyl)carbamoyl, di-($C_{1-4}$alkyl)carbamoyl, phenylcarbamoyl, $C_{1-4}$alkylsulfonyl, phenylsulfonyl, sulfamoyl, $C_{1-4}$alkylsulfamoyl, di-$C_{1-4}$alkylsulfamoyl or phenylsulfamoyl, wherein M is hydrogen or a non-chromophoric cation, each of $R_3$ and $R_4$ is independently hydrogen; $C_{1-8}$alkyl; $C_{1-8}$alkyl monosubstituted by hydroxy, chloro, bromo, cyano, thiocyano, ($C_{1-4}$alkyl)carbonyl, ($C_{1-4}$alkoxy)carbonyl, formyloxy, ($C_{1-4}$alkyl)carbonyloxy, ($C_{1-4}$chloroalkyl)carbonyloxy, ($C_{1-4}$bromoalkyl)carbonyloxy, ($C_{1-4}$alkoxy)carbonyloxy, ($C_{1-4}$alkoxy)($C_{1-4}$alkoxy)carbonyl, allyloxycarbonyl, chloroallyloxycarbonyl, bromoallyloxycarbonyl, $C_{2-4}$alkenyloxy, $C_{2-4}$chloroalkenyloxy, $C_{2-4}$bromoalkenyloxy, $C_{2-4}$alkynyloxy, benzoyloxy, $C_{1-4}$alkoxy, phenyl, phenoxy, phenyl($C_{1-4}$alkoxy), ($C_{1-4}$alkyl)carbamoyl, di-($C_{1-4}$alkyl)carbamoyl, ($C_{1-4}$alkyl)carbamoyloxy, di-($C_{1-4}$alkyl)carbamoyloxy, phenylcarbamoyl, phenylcarbamoyloxy, phthalimidyl, saccharinyl-2, pyridyl or benzothiazolyl-2-mercapto; ($C_{1-4}$-alkoxy)$C_{1-4}$alkyl the $C_{1-4}$alkoxy moiety of which is monosubstituted by hydroxy, chloro, bromo, cyano, $C_{1-4}$alkoxy, ($C_{1-4}$alkoxy)carbonyl, ($C_{1-4}$alkoxy)carbonyloxy or ($C_{1-4}$alkyl)carbonyloxy; 2-hydroxy-3-propynyloxypropyl; 2-($C_{1-4}$alkyl)carbonyloxy-3-propynyloxypropyl; 2-hydroxy-3-allyloxypropyl; 2-($C_{1-4}$alkyl)carbonyloxy-3-allyloxypropyl; $C_{2-4}$alkenyl; $C_{2-4}$alkenyl monosubstituted by phenyl, chloro or bromo; $C_{2-4}$alkynyl; $C_{5-7}$cycloalkyl; $C_{5-7}$cycloalkyl substituted by 1 to 3 methyl groups; phenyl or substituted phenyl having 1 to 3 substituents each of which is independently chloro, bromo, methyl or $C_{1-2}$alkoxy, with the provisos that at least one of $R_3$ and $R_4$ is other than $C_{5-7}$cycloalkyl, $C_{5-7}$cycloalkyl substituted by 1 to 3 methyl groups, phenyl or substituted phenyl and that at least one of $R_3$ and $R_4$ is other than hydrogen, $R_5$ is hydrogen, chloro, bromo, $C_{1-2}$alkyl, $C_{1-2}$alkoxy or phenoxy, and $R_6$ is hydrogen; $C_{1-2}$alkyl; $C_{1-2}$alkoxy; cyano; formamido; ($C_{1-4}$alkyl)carbonylamino; ($C_{1-4}$alkyl)carbonylamino the $C_{1-4}$alkyl moiety of which is monosubstituted by hydroxy, chloro, bromo, $C_{1-4}$alkoxy, phenyl or phenoxy; benzamido; ($C_{2-4}$alkenyl)carbonylamino; aminocarbonylamino; ($C_{1-4}$alkyl)aminocarbonylamino; ($C_{1-4}$alkoxy)carbonylamino; ($C_{1-4}$alkoxy)carbonylamino the $C_{1-4}$alkoxy moiety of which is monosubstituted by $C_{1-4}$alkoxy or phenyl; $C_{1-2}$alkylsulfonylamino; phenylsulfonylamino; di-$C_{1-2}$alkylaminosulfonylamino; chloro; bromo or phenoxy, with the proviso that $R_6$ is other than chloro, bromo or phenoxy when $R_5$ is chloro, bromo or phenoxy, with the proviso that the molecule is free of metallizable groups and

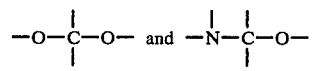

radicals.

2. A compound according to claim 1 wherein $R_1'$ is hydrogen; $C_{1-2}$alkyl; $C_{1-2}$alkyl monosubstituted by chloro, phenyl, chlorophenyl, dichlorophenyl, cyano, acetoxy, benzoyl, ($C_{1-2}$alkyl)carbonyl or carbamoyl; allyl; 3-chloroallyl; 3-phenylallyl; phenyl; chlorophenyl or tolyl.

3. A compound according to claim 1 wherein $R_2'$ is cyano, nitro, —COOM, acetyl, ($C_{1-2}$alkoxy)carbonyl, carbamoyl, thiocyano or methylsulfonyl, wherein M is hydrogen or a non-chromophoric cation.

4. A compound according to claim 1 wherein each of $R_3$ and $R_4$ is independently hydrogen; $C_{1-4}$alkyl; $C_{1-4}$alkyl monosubstituted by chloro, hydroxy, cyano, thiocyano, ($C_{1-2}$alkyl)carbonyl, formyloxy, ($C_{1-2}$alkyl)carbonyloxy, ($C_{1-2}$chloroalkyl)carbonyloxy, allyloxy, 3-chloroallyloxy, 3-bromoallyloxy, prop-2-ynyloxy, ($C_{1-2}$alkoxy)carbonyl, benzoyloxy, ($C_{1-2}$alkoxy)carbonyloxy, allyloxycarbonyl, chloroallyloxycarbonyl, methoxyethoxycarbonyl, phenylcarbamoyloxy, $C_{1-3}$alkoxy, phenyl($C_{1-2}$alkoxy), ($C_{1-2}$alkoxy)carbonyl($C_{1-2}$alkoxy), chloroethoxy, cyano($C_{1-2}$alkoxy) or diethylcarbamoyl; 2-hydroxy-3-prop-2-ynyloxypropyl; 2-acetoxy-3-prop-2-ynyloxypropyl; allyl; 2-methylallyl; 3-chloroallyl; 3-phenylallyl; prop-2-ynyl; cylcohexyl; phenyl or benzyl, with the provisos that at least one of $R_3$ and $R_4$ is other than cyclohexyl, phenyl or benzyl and at least one of $R_3$ and $R_4$ is other than hydrogen.

5. A compound according to claim 1 wherein $R_5$ is hydrogen, chloro, methyl or $C_{1-2}$alkoxy, and $R_6$ is hydrogen, methyl, ($C_{1-2}$alkyl)carbonylamino, ($C_{1-2}$chloroalkyl)carbonylamino, benzamido, ($C_{1-2}$alkoxy)carbonylamino, ($C_{1-2}$alkoxy)ethoxycarbonylamino, methylsulfonylamino, dimethylaminosulfonylamino, crotonoylamino, aminocarbonylamino or ethylaminocarbonylamino.

6. A compound according to claim 1 wherein $R_5$ is hydrogen, chloro, methyl or $C_{1-2}$alkoxy.

7. A compound according to claim 1 wherein $R_6$ is hydrogen, methyl, ($C_{1-2}$alkyl)carbonylamino, ($C_{1-2}$chloroalkyl)carbonylamino, benzamido, ($C_{1-2}$alkoxy)carbonylamino, ($C_{1-2}$alkoxy)ethoxycarbonylamino, methylsulfonylamino, dimethylaminosulfonylamino, crotonoylamino, aminocarbonylamino or ethylaminocarbonylamino.

8. A compound according to claim 1 wherein
$R_1'$ is hydrogen; $C_{1-2}$alkyl; $C_{1-2}$alkyl monosubstituted by chloro, phenyl, chlorophenyl, dichlorophenyl, cyano, acetoxy, benzoyl, ($C_{1-2}$alkyl)carbonyl or carbamoyl; allyl; 3-chloroallyl; 3-phenylallyl; phenyl; chlorophenyl or tolyl,
$R_2'$ is cyano, nitro, —COOM, acetyl, ($C_{1-2}$alkoxy)carbonyl, carbamoyl, thiocyano or methylsulfonyl, wherein M is hydrogen or a non-chromophoric cation,
each of $R_3$ and $R_4$ is independently $C_{2-4}$alkyl; $C_{2-4}$alkyl monosubstituted by chloro, hydroxy, $C_{1-2}$alkoxy, cyano(C$_{1-2}$alkoxy), chloroethoxy, (C$_{1-2}$alkoxy)carbonylethoxy, allyloxy, prop-2-ynyloxy, benzyloxy, cyano, (C$_{1-2}$alkyl)carbonyloxy, (C$_{1-2}$alkoxy)carbonyl or (C$_{1-2}$alkoxy)carbonyloxy; benzyl; allyl; 2-methylallyl; 3-chloroallyl; 3-phenylallyl or prop-2-ynyl, with the proviso that at least one of R$_3$ and R$_4$ is other than benzyl, R$_5$ is hydrogen or C$_{1-2}$alkoxy, and R$_6$ is hydrogen, methyl or (C$_{1-2}$alkyl)carbonylamino.

9. A compound according to claim 8 wherein
R$_1'$ is phenyl, chlorophenyl, benzyl, chlorobenzyl, dichlorobenzyl or tolyl, R$_2'$ is cyano, carbamoyl or (C$_{1-2}$alkoxy)carbonyl, and each of R$_3$ and R$_4$ is independently acetoxyethyl, allyloxyethyl, prop-2-ynyloxyethyl, 2-acetoxypropyl, allyl, 2-methylallyl or benzyloxyethyl.

10. A compound according to claim 9 wherein
R$_1'$ is benzyl, chlorobenzyl or dichlorobenzyl, R$_2'$ is cyano, each of R$_3$ and R$_4$ is independently acetoxyethyl, allyloxyethyl, 2-acetoxypropyl, allyl or 2-methylallyl, R$_5$ is hydrogen, and R$_6$ is acetamido.

11. A compound according to claim 8 wherein
R$_1'$ is benzyl, chlorobenzyl or dichlorobenzyl, R$_2'$ is cyano, R$_5$ is hydrogen, and R$_6$ is acetamido.

12. A process for dyeing or printing a hydrophobic, synthetic or semi-synthetic high molecular weight organic textile substrate comprising exhaust dyeing, pad dyeing or printing a hydrophobic, synthetic or semi-synthetic high molecular weight organic textile substrate with a disperse compound according to claim 1.

13. A compound according to claim 1 wherein R$_1'$ is C$_{1-4}$alkyl; C$_{1-4}$alkyl monosubstituted by fluoro, bromo, chloro, hydroxy, (C$_{1-4}$alkyl)carbonyl, C$_{1-4}$alkoxy, cyano, thiocyano, phenoxy, (C$_{1-4}$alkoxy)carbonyl, phenoxycarbonyl, (C$_{1-4}$alkoxy)ethoxycarbonyl, carbamoyl, (C$_{1-4}$alkyl)carbamoyl, di-(C$_{1-4}$alkyl)carbamoyl, phenylcarbamoyl, N-C$_{1-4}$alkyl-N-phenylcarbamoyl, benzoyl, (C$_{1-4}$alkyl)carbonyloxy, phenylsulfonyl, C$_{1-4}$alkylsulfonyl, sulfamoyl, C$_{1-4}$alkylsulfamoyl, di-C$_{1-4}$alkylsulfamoyl, phenylsulfamoyl, N-C$_{1-4}$alkyl-N-phenylsulfamoyl, phenyl or substituted phenyl having 1 to 2 substituents each of which is independently chloro, bromo, nitro, cyano, trifluoromethyl, C$_{1-4}$alkyl or C$_{1-4}$alkoxy; C$_{2-4}$alkenyl; C$_{2-4}$alkenyl monosubstituted by chloro, bromo or phenyl; phenyl or substituted phenyl having 1 to 3 substituents each of which is independently C$_{1-4}$alkyl, C$_{1-4}$alkoxy, chloro, bromo, nitro, cyano (maximum of two), trifluoromethyl (maximum of two), (C$_{1-4}$alkoxy)carbonyl (maximum of two), formyl (maximum of one), (C$_{1-4}$alkyl)carbonyl (maximum of one), carbamoyl (maximum of one), (C$_{1-4}$alkyl)carbamoyl (maximum of one), di-(C$_{1-4}$alkyl)carbamoyl (maximum of one), C$_{1-4}$alkylsulfonyl (maximum of one), phenylsulfonyl (maximum of one), sulfamoyl (maximum of one), C$_{1-4}$alkylsulfamoyl (maximum of one), di-C$_{1-4}$alkylsulfamoyl (maximum of one) or phenylsulfamoyl (maximum of one).

14. A compound according to claim 2 wherein R$_1'$ is C$_{1-2}$alkyl; C$_{1-2}$alkyl monosubstituted by chloro, phenyl, chlorophenyl, dichlorophenyl, cyano, acetoxy, benzoyl, (C$_{1-2}$alkyl)carbonyl or carbamoyl; allyl; 3-chloroallyl; 3-phenylallyl; phenyl; chlorophenyl or tolyl.

15. A compound according to claim 8 wherein R$_1'$ is C$_{1-2}$alkyl; C$_{1-2}$alkyl monosubstituted by chloro, phenyl, chlorophenyl, dichlorophenyl, cyano, acetoxy, benzoyl, (C$_{1-2}$alkyl)carbonyl or carbamoyl, allyl; 3-chloroallyl; 3-phenylallyl; phenyl; chlorophenyl or tolyl.

16. The compound according to claim 9 having the formula

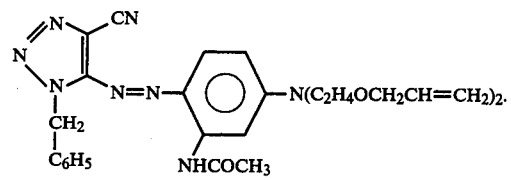

17. The compound according to claim 9 having the formula

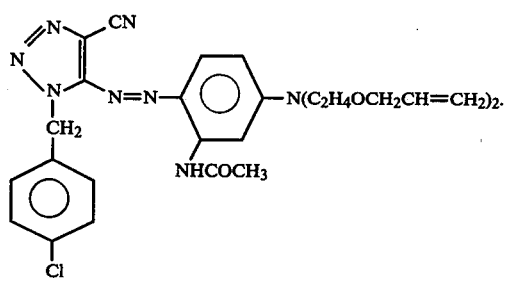

18. The compound according to claim 9 having the formula

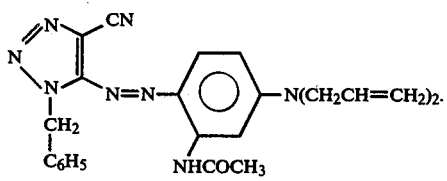

19. The compound according to claim 9 having the formula

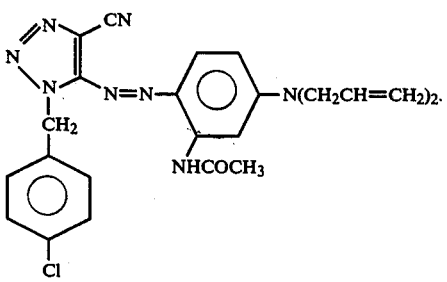

20. The compound according to claim 9 having the formula

21. The compound according to claim 9 having the formula
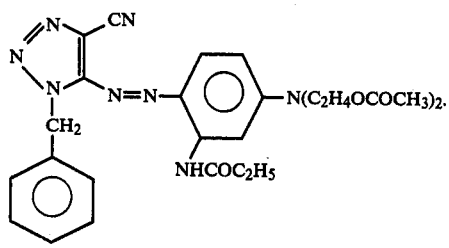
22. The compound according to claim 9 having the formula
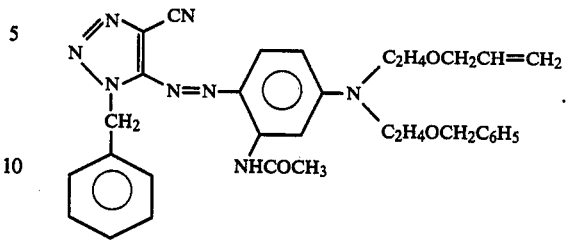
23. The compound according to claim 9 having the formula
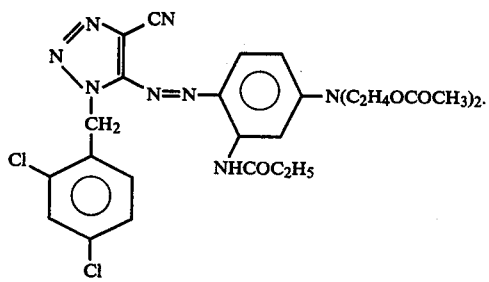
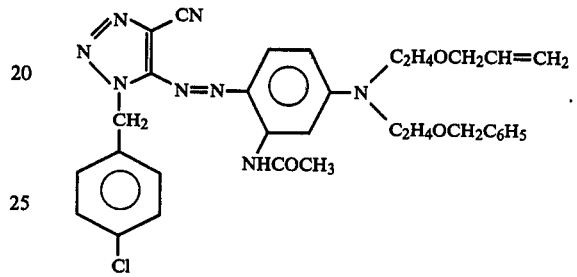
* * * * *